United States Patent [19]
Vinik et al.

[11] Patent Number: 5,834,590
[45] Date of Patent: Nov. 10, 1998

[54] INGAP PROTEIN INVOLVED IN PANCREATIC ISLET NEOGENESIS

[75] Inventors: Aaron I. Vinik, Norfolk; Gary L. Pittenger, Virginia Beach; Ronit Rafaeloff, Norfolk, all of Va.; Lawrence Rosenberg; William P. Duguid, both of Montreal, Canada

[73] Assignee: Eastern Virginia Medical School of the Medical College of Hampton Roads, Norfolk, Va.

[21] Appl. No.: 401,530

[22] Filed: Feb. 22, 1995

[51] Int. Cl.$^6$ ........................................... C07K 14/00
[52] U.S. Cl. ........................... 530/350; 530/412; 514/12; 514/13; 514/14; 424/198.1; 435/69.7
[58] Field of Search ...................... 530/350, 412; 514/12, 13, 14; 424/198.1; 435/69.7

[56] References Cited

U.S. PATENT DOCUMENTS 4,965,188  10/1990  Mullis et al. .

OTHER PUBLICATIONS

Stein et al., "Antisense Oligonucleotides as Therapeutic Agent—Is the Bullet Really Magical?", *Science* 261: 1004–1012 (1993).

Bradley et al., "BoiTechnology. Modifying the Mouse", *Design and Desire* 10:534–539 (1992).

Miller et al., "Human Gene Therapy Comes of Age", *Nature* 357:455–460 (1992).

Watanabe et al., "Pancreatic Beta–Cell Replication and Amelioration of Surgical Diabetes by Reg Protein", *Proc. Natl. Acad. Sci. USA* 91:3589–3592 (1994).

Liang et al., "Distribution and Cloning of Eukaryotic mRNAs by Means of Differential Display: Refinements and Optimization", *Nucleic Acids Research* 21(14):3269–3275 (1993).

Rosenberg et al., "Reversal of Diabetes by the Induction of Islet Cell Neogenesis", *Transplantation Proceedings* 24(3):1027–1028 (1992).

Rosenberg L. et al. (1992) Pancreatic Islet Cell Regeneration and Growth. ed. Al Vinik, Plenum Press, New York, pp. 95–104, 1992.

Pittenger GL. et al. (1992) The Partial Isolation and Characterization of Ilotropin, a Novel Islet–Specific Growth Factor (abstract) Adv Exp Med Biol 321, pp. 123–132, 1992.

Rouquier et al., "Rat Pancreatic Stone Protein Messenger RNA", *J. Biol. Chem.*, 266(2):786–791 (1991).

Lasserre et al., "A Novel Gene (HIP) Activated in Human Primary Liver Cancer", *Cancer Research* 52:5089–5095 (1992).

Terazono et al., "A Novel Gene Activated in Regenerating Islets", *J. Biol. Chem.*, 263(5):211–2114 (1988).

Vinik et al., "Factors Controlling Pancreatic Islet Neogenesis", *Yale Journal of Biology and Medicine* 65:471–491 (1992).

Orelle et al., "Human Pancreatitis–associated Protein" *J. Clin. Invest.* 90:2284–2291 (1992).

*Primary Examiner*—Robert A. Wax
*Assistant Examiner*—Enrique D. Longton
*Attorney, Agent, or Firm*—Banner & Witcoff, Ltd.

[57] ABSTRACT

Cellophane wrapping (CW) of hamster pancreas induces proliferation of duct epithelial cells followed by endocrine cell differentiation and islet neogenesis. Using the mRNA differential display technique a cDNA clone expressed in cellophane wrapped but not in control pancreata was identified. Using this cDNA as a probe, a cDNA library was screened and a gene not previously described was identified and named INGAP.

24 Claims, 4 Drawing Sheets

FIG. 1A

```
CTGCAAGACA GGTACCATG ATG CTT CCC ATG ACC CTC TGT AGG ATG TCT TGG       52
                    Met Leu Pro Met Thr Leu Cys Arg Met Ser Trp
                     1                   5                   10

ATG CTG CTT TCC TGC CTG ATG TTC CTT TCT TGG GTG GAA GGT GAA GAA       100
Met Leu Leu Ser Cys Leu Met Phe Leu Ser Trp Val Glu Gly Glu Glu
                15                  20                  25

TCT CAA AAG AAA CTG CCT TCT TCA CGT ATA ACC TGT CCT CAA GGC TCT       148
Ser Gln Lys Lys Leu Pro Ser Ser Arg Ile Thr Cys Pro Gln Gly Ser
            30                  35                  40

GTA GCC TAT GGG TCC TAT TGC CAG TAT TCA CTG ATT TTG ATA CCA CAG ACC   196
Val Ala Tyr Gly Ser Tyr Cys Gln Tyr Ser Leu Ile Leu Ile Pro Gln Thr
        45                  50                  55

TGG TCT AAT GCA GAA CTA TCC TGC CAG ATG CAT TTC TCA GGA CAC CTG       244
Trp Ser Asn Ala Glu Leu Ser Cys Gln Met His Phe Ser Gly His Leu
    60                  65                  70                  75

GCA TTT CTT CTC AGT ACT GGT GAA ATT ACC TTC GTG TCC TCC CTT GTG       292
Ala Phe Leu Leu Ser Thr Gly Glu Ile Thr Phe Val Ser Ser Leu Val
                80                  85                  90

AAG AAC AGT TTG ACG GCC TAC CAG TAC ATC TGG ATT GGA CTC CAT GAT       340
Lys Asn Ser Leu Thr Ala Tyr Gln Tyr Ile Trp Ile Gly Leu His Asp
            95                  100                 105
```

FIG. 1B

```
CCC TCA CAT GGT ACA CTA CCC AAC GGA AGT GGA TGG AAG TGG AGC AGT       388
Pro Ser His Gly Thr Leu Pro Asn Gly Ser Gly Trp Lys Trp Ser Ser
        110                     115                     120

TCC AAT GTG CTG ACC TTC TAT AAC TGG GAG AGG AAC CCC TCT ATT GCT       436
Ser Asn Val Leu Thr Phe Tyr Asn Trp Glu Arg Asn Pro Ser Ile Ala
        125                     130                     135

GCT GAC CGT GGT TAT TGT GCA GTT TTG TCT CAG AAA TCA GGT TTT CAG       484
Ala Asp Arg Gly Tyr Cys Ala Val Leu Ser Gln Lys Ser Gly Phe Gln
        140                     145                     150                155

AAG TGG AGA GAT TTT AAT TGT GAA AAT GAG CTT CCC TAT ATC TGC AAA       532
Lys Trp Arg Asp Phe Asn Cys Glu Asn Glu Leu Pro Tyr Ile Cys Lys
        160                     165                     170

TTC AAG GTC TAGGGCAGTT CTAATTTCAA CAGCTTGAAA ATATTATGAA               581
Phe Lys Val

GCTCACATGG ACAAGGAAGC AAGTATGAGG ATTCACTCAG GAAGAGCAAG CTCTGCCTAC     641

ACACCCACAC CAATTCCCTT ATATCATCTC TGCTGTTTTT CTATCAGTAT ATTCTGTGGT     701

GGCTGTAACC TAAAGGCTCA GAGAACAAAA ATAAAATGTC ATCAAC                    747
```

FIG. 2

```
INGAP        MLPMTLC-RMSWMLLSCLMFLSWVEGEESQKKLPSS              35
PAP-I        MLHRLAFPVMSWMLLSCLMLLSQVQGEDSPKKIPSA              36
PAP-H/HIP    MLPPMALPSVSWMLLSCLMLLSQVQGEEPQRELPSA              36
PAP-III      MLPRVALTTMSWMLLSSLMLLSQVQGEDAKEDVPTS              36
PAP-II       MLPRLSFNNVSWTLLYYLFIF-QVRGEDSQKAVPST              35
REG/LITH     ----MT-RNKYFILLSCLMVLSPSQGQEAEEDLPSA              31
"DRICKAMER"

*              *                  *
INGAP        RITCPQGSVAYGSYCYSLILIPQTWSNAELSCQMHF              71
PAP-I        RISCPKGSQAYGSYCYALFQIPQTWFDAELACQKRP              72
PAP-H/HIP    RIRCPKGSKAYGSHCYALFLSPKSWTDADLACQKRP              72
PAP-III      RISCPKGSRAYGSYCYALFSVKSWFDADLACQKRP               72
PAP-II       RTSCPMGSKAYRSYCYTLVTTLKSWFQADLACQKRP              71
REG/LITH     RITCPEGSNAYSSYCYYFMEDHLSWAEADLFCQNMN              67
"DRICKAMER"        G                                C

INGAP        SGHLAFLLSTGEITFVSSLVKNSLTAYQYIWIGLHD             107
PAP-I        EGHLVSVLNVAEASFLASMVKNTGNSYQYIWIGLHD             108
PAP-H/HIP    SGNLVSVLSGAEGSFVSSLVKSIGNSYSYVWIGLHD             108
PAP-III      SGHLVSVLSGSEASFVSSLIKSSGNSGQNVWIGLHD             108
PAP-II       SGHLVSILSGGEASFVSSLVTGRVNNQDIWIWLHD              107
REG/LITH     SGYLVSVLSQAEGNFLASLIKESGTTAANVWIGLHD             103
"DRICKAMER"                                     G  TD

INGAP        PSHGTLPNGSGWKWSSSNVLTFYNWERNPSIAADRG             143
PAP-I        PTLGGEPNGGGWEWSNNDIMNYVNWERNPSTALDRG             144
PAP-H/HIP    PTQGTEPNGEGWEWSSSDVMNYFAWERNPSTISSPG             144
PAP-III      PTLGQEPNRGGWEWSNADVMNYFNWETNPSSVSGS-             143
PAP-II       PTMGQQPNGGGWEWSNSDVLNYLNWGDPSSTVNRG              143
REG/LITH     P------KNNRRWHWSSGSLFLYKSWDTGYPNNSNRG            134
"DRICKAMER"            T       W       P          G
                   *              *         *
INGAP        YCAVLSQKSGFQKWRDFNCENELPYICKFKV                  175
PAP-I        FCGSLSRSSGFLRWRDTTCEVKLPYVCKFTG                  176
PAP-H/HIP    HCASLSRSTAFLRWKDYNCNVRLPYVCKFTD                  176
PAP-III      HCGTLTRASGFLRWRENNCISELPYVCKFKA                  175
PAP-II       NCGSLTATSEFLKWGDHHCDVELPFVCKFKQ                  175
REG/LITH     YCVSVTSNSGYKKWRDNSCDAQLSFVCKFKA                  165
"DRICKAMER"  EC       G       WND C            CE
```

← 0.9 kb

← 1.6 kb

← 18s

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 747 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Cricetulus ( i x ) FEATURE:
( A ) NAME/KEY: CDS
( B ) LOCATION: 20..541

( x i ) SEQUENCE DESCRIPTION: SEQ ID NO:1:

```
CTGCAAGACA GGTACCATG ATG CTT CCC ATG ACC CTC TGT AGG ATG TCT TGG              52
                    Met Leu Pro Met Thr Leu Cys Arg Met Ser Trp
                     1               5                      10

ATG CTG CTT TCC TGC CTG ATG TTC CTT TCT TGG GTG GAA GGT GAA GAA              100
Met Leu Leu Ser Cys Leu Met Phe Leu Ser Trp Val Glu Gly Glu Glu
              15                  20                      25

TCT CAA AAG AAA CTG CCT TCT TCA CGT ATA ACC TGT CCT CAA GGC TCT              148
Ser Gln Lys Lys Leu Pro Ser Ser Arg Ile Thr Cys Pro Gln Gly Ser
         30                      35                  40

GTA GCC TAT GGG TCC TAT TGC TAT TCA CTG ATT TTG ATA CCA CAG ACC              196
Val Ala Tyr Gly Ser Tyr Cys Tyr Ser Leu Ile Leu Ile Pro Gln Thr
     45                  50                      55

TGG TCT AAT GCA GAA CTA TCC TGC CAG ATG CAT TTC TCA GGA CAC CTG              244
Trp Ser Asn Ala Glu Leu Ser Cys Gln Met His Phe Ser Gly His Leu
 60                  65                      70                      75

GCA TTT CTT CTC AGT ACT GGT GAA ATT ACC TTC GTG TCC TCC CTT GTG              292
Ala Phe Leu Leu Ser Thr Gly Glu Ile Thr Phe Val Ser Ser Leu Val
                 80                      85                  90

AAG AAC AGT TTG ACG GCC TAC CAG TAC ATC TGG ATT GGA CTC CAT GAT              340
Lys Asn Ser Leu Thr Ala Tyr Gln Tyr Ile Trp Ile Gly Leu His Asp
             95                     100                 105

CCC TCA CAT GGT ACA CTA CCC AAC GGA AGT GGA TGG AAG TGG AGC AGT              388
Pro Ser His Gly Thr Leu Pro Asn Gly Ser Gly Trp Lys Trp Ser Ser
         110                     115                 120

TCC AAT GTG CTG ACC TTC TAT AAC TGG GAG AGG AAC CCC TCT ATT GCT              436
Ser Asn Val Leu Thr Phe Tyr Asn Trp Glu Arg Asn Pro Ser Ile Ala
     125                     130                 135

GCT GAC CGT GGT TAT TGT GCA GTT TTG TCT CAG AAA TCA GGT TTT CAG              484
```

| | | | | | | | | | | | | | | | | |
|---|---|---|---|---|---|---|---|---|---|---|---|---|---|---|---|---|
| Ala | Asp | Arg | Gly | Tyr | Cys | Ala | Val | Leu | Ser | Gln | Lys | Ser | Gly | Phe | Gln | |
| 140 | | | | 145 | | | | | 150 | | | | | 155 | | |

| | | | | | | | | | | | | | | |
|---|---|---|---|---|---|---|---|---|---|---|---|---|---|---|
| AAG | TGG | AGA | GAT | TTT | AAT | TGT | GAA | AAT | GAG | CTT | CCC | TAT | ATC | TGC | AAA | 532 |
| Lys | Trp | Arg | Asp | Phe | Asn | Cys | Glu | Asn | Glu | Leu | Pro | Tyr | Ile | Cys | Lys | |
| | | | 160 | | | | | 165 | | | | | 170 | | |

TTC AAG GTC TAGGGCAGTT CTAATTTCAA CAGAGAGCAA GCTCTGCCTA CACACCCACA 591
Phe Lys Val

CCAATTCCCT TATATCATCT CTGCTGTTTT TCCTTGAAAT TATTATGAAG CTCACATGGA 651

CAAGGAAGCA AGTATGAGGA TTCACTCAGG ATATCAGTAT ATTCTGTGGT GGCTGTAACC 711

TAAAGGCTCA GAGAACAAAA ATAAAATGTC ATCAAC 747

(2) INFORMATION FOR SEQ ID NO:2:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Leu | Pro | Met | Thr | Leu | Cys | Arg | Met | Ser | Trp | Met | Leu | Leu | Ser | Cys |
| 1 | | | | 5 | | | | | 10 | | | | | 15 | |
| Leu | Met | Phe | Leu | Ser | Trp | Val | Glu | Gly | Glu | Ser | Gln | Lys | Lys | Leu | |
| | | | 20 | | | | | 25 | | | | | 30 | | |
| Pro | Ser | Ser | Arg | Ile | Thr | Cys | Pro | Gln | Gly | Ser | Val | Ala | Tyr | Gly | Ser |
| | | | 35 | | | | 40 | | | | | 45 | | | |
| Tyr | Cys | Tyr | Ser | Leu | Ile | Leu | Ile | Pro | Gln | Thr | Trp | Ser | Asn | Ala | Glu |
| | 50 | | | | | 55 | | | | | 60 | | | | |
| Leu | Ser | Cys | Gln | Met | His | Phe | Ser | Gly | His | Leu | Ala | Phe | Leu | Leu | Ser |
| 65 | | | | | 70 | | | | | 75 | | | | | 80 |
| Thr | Gly | Glu | Ile | Thr | Phe | Val | Ser | Ser | Leu | Val | Lys | Asn | Ser | Leu | Thr |
| | | | | 85 | | | | | 90 | | | | | 95 | |
| Ala | Tyr | Gln | Tyr | Ile | Trp | Ile | Gly | Leu | His | Asp | Pro | Ser | His | Gly | Thr |
| | | | 100 | | | | | 105 | | | | | 110 | | |
| Leu | Pro | Asn | Gly | Ser | Gly | Trp | Lys | Trp | Ser | Ser | Ser | Asn | Val | Leu | Thr |
| | | | 115 | | | | | 120 | | | | | 125 | | |
| Phe | Tyr | Asn | Trp | Glu | Arg | Asn | Pro | Ser | Ile | Ala | Ala | Asp | Arg | Gly | Tyr |
| | | | 130 | | | | | 135 | | | | | 140 | | |
| Cys | Ala | Val | Leu | Ser | Gln | Lys | Ser | Gly | Phe | Gln | Lys | Trp | Arg | Asp | Phe |
| 145 | | | | | 150 | | | | | 155 | | | | | 160 |
| Asn | Cys | Glu | Asn | Glu | Leu | Pro | Tyr | Ile | Cys | Lys | Phe | Lys | Val | | |
| | | | | 165 | | | | | 170 | | | | | | |

(2) INFORMATION FOR SEQ ID NO:3:

(i) SEQUENCE CHARACTERISTICS:
        (A) LENGTH: 175 amino acids
        (B) TYPE: amino acid
        (D) TOPOLOGY: linear (ii) MOLECULE TYPE: protein (iv) ANTI-SENSE: NO (vi) ORIGINAL SOURCE:
        (A) ORGANISM: Rattus rattus (xi) SEQUENCE DESCRIPTION: SEQ ID NO:3:

| | | | | | | | | | | | | | | | |
|---|---|---|---|---|---|---|---|---|---|---|---|---|---|---|---|
| Met | Leu | His | Arg | Leu | Ala | Phe | Pro | Val | Met | Ser | Trp | Met | Leu | Leu | Ser |
| 1 | | | | 5 | | | | | 10 | | | | | 15 | |

| | | | | | | | | | | | | | | |
|---|---|---|---|---|---|---|---|---|---|---|---|---|---|---|
|Cys|Leu|Met|Leu<br>20|Leu|Ser|Gln|Val|Gln<br>25|Gly|Glu|Asp|Ser|Pro<br>30|Lys|Lys|
|Ile|Pro|Ser<br>35|Ala|Arg|Ile|Ser|Cys<br>40|Pro|Lys|Gly|Ser|Gln<br>45|Ala|Tyr|Gly|
|Ser|Tyr<br>50|Cys|Tyr|Ala|Leu|Phe<br>55|Gln|Ile|Pro|Gln|Thr<br>60|Trp|Phe|Asp|Ala|
|Glu<br>65|Leu|Ala|Cys|Gln|Lys<br>70|Arg|Pro|Glu|Gly|His<br>75|Leu|Val|Ser|Val|Leu<br>80|
|Asn|Val|Ala|Glu|Ala<br>85|Ser|Phe|Leu|Ala|Ser<br>90|Met|Val|Lys|Asn|Thr<br>95|Gly|
|Asn|Ser|Tyr|Gln<br>100|Tyr|Ile|Trp|Ile|Gly<br>105|Leu|His|Asp|Pro|Thr<br>110|Leu|Gly|
|Gly|Glu|Pro<br>115|Asn|Gly|Gly|Gly|Trp<br>120|Glu|Trp|Ser|Asn|Asn<br>125|Asp|Ile|Met|
|Asn|Tyr<br>130|Val|Asn|Trp|Glu|Arg<br>135|Asn|Pro|Ser|Thr|Ala<br>140|Leu|Asp|Arg|Gly|
|Phe<br>145|Cys|Gly|Ser|Leu|Ser<br>150|Arg|Ser|Ser|Gly|Phe<br>155|Leu|Arg|Trp|Arg|Asp<br>160|
|Thr|Thr|Cys|Glu|Val<br>165|Lys|Leu|Pro|Tyr|Val<br>170|Cys|Lys|Phe|Thr|Gly<br>175| |

( 2 ) INFORMATION FOR SEQ ID NO:4:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO:4:

| | | | | | | | | | | | | | | |
|---|---|---|---|---|---|---|---|---|---|---|---|---|---|---|
|Met<br>1|Leu|Pro|Pro|Met<br>5|Ala|Leu|Pro|Ser|Val<br>10|Ser|Trp|Met|Leu|Leu<br>15|Ser|
|Cys|Leu|Met|Leu<br>20|Leu|Ser|Gln|Val|Gln<br>25|Gly|Glu|Glu|Pro|Gln<br>30|Arg|Glu|
|Leu|Pro|Ser<br>35|Ala|Arg|Ile|Arg|Cys<br>40|Pro|Lys|Gly|Ser|Lys<br>45|Ala|Tyr|Gly|
|Ser|His<br>50|Cys|Tyr|Ala|Leu|Phe<br>55|Leu|Ser|Pro|Lys|Ser<br>60|Trp|Thr|Asp|Ala|
|Asp<br>65|Leu|Ala|Cys|Gln|Lys<br>70|Arg|Pro|Ser|Gly|Asn<br>75|Leu|Val|Ser|Val|Leu<br>80|
|Ser|Gly|Ala|Glu|Gly<br>85|Ser|Phe|Val|Ser|Ser<br>90|Leu|Val|Lys|Ser|Ile<br>95|Gly|
|Asn|Ser|Tyr|Ser<br>100|Tyr|Val|Trp|Ile|Gly<br>105|Leu|His|Asp|Pro|Thr<br>110|Gln|Gly|
|Thr|Glu|Pro<br>115|Asn|Gly|Glu|Gly|Trp<br>120|Glu|Trp|Ser|Ser|Ser<br>125|Asp|Val|Met|
|Asn|Tyr<br>130|Phe|Ala|Trp|Glu|Arg<br>135|Asn|Pro|Ser|Thr|Ile<br>140|Ser|Ser|Pro|Gly|
|His<br>145|Cys|Ala|Ser|Leu|Ser<br>150|Arg|Ser|Thr|Ala|Phe<br>155|Leu|Arg|Trp|Lys|Asp<br>160|
|Tyr|Asn|Cys|Asn|Val<br>165|Arg|Leu|Pro|Tyr|Val<br>170|Cys|Lys|Phe|Thr|Asp<br>175| |

(2) INFORMATION FOR SEQ ID NO:5:

(i) SEQUENCE CHARACTERISTICS:
        (A) LENGTH: 174 amino acids
        (B) TYPE: amino acid
        (D) TOPOLOGY: linear (ii) MOLECULE TYPE: protein (vi) ORIGINAL SOURCE:
        (A) ORGANISM: Rattus rattus (xi) SEQUENCE DESCRIPTION: SEQ ID NO:5:

```
Met Leu Pro Arg Val Ala Leu Thr Thr Met Ser Trp Met Leu Leu Ser
 1               5                  10                  15
Ser Leu Met Leu Leu Ser Gln Val Gln Gly Glu Asp Ala Lys Glu Asp
            20                  25                  30
Val Pro Thr Ser Arg Ile Ser Cys Pro Lys Gly Ser Arg Ala Tyr Gly
                35                  40                  45
Ser Tyr Cys Tyr Ala Leu Phe Ser Val Ser Lys Ser Trp Phe Asp Ala
        50                  55                  60
Asp Leu Ala Cys Gln Lys Arg Pro Ser Gly His Leu Val Ser Val Leu
 65                  70                  75                  80
Ser Gly Ser Glu Ala Ser Phe Val Ser Ser Leu Ile Lys Ser Ser Gly
                85                  90                  95
Asn Ser Gly Gln Asn Val Trp Ile Gly Leu His Asp Pro Thr Leu Gly
            100                 105                 110
Gln Glu Pro Asn Arg Gly Gly Trp Glu Trp Ser Asn Ala Asp Val Met
            115                 120                 125
Asn Tyr Phe Asn Trp Glu Thr Asn Pro Ser Ser Val Ser Gly Ser His
        130                 135                 140
Cys Gly Thr Leu Thr Arg Ala Ser Gly Phe Leu Arg Trp Arg Glu Asn
145                 150                 155                 160
Asn Cys Ile Ser Glu Leu Pro Tyr Val Cys Lys Phe Lys Ala
                165                 170
```

(2) INFORMATION FOR SEQ ID NO:6:

(i) SEQUENCE CHARACTERISTICS:
        (A) LENGTH: 174 amino acids
        (B) TYPE: amino acid
        (D) TOPOLOGY: linear (ii) MOLECULE TYPE: protein (vi) ORIGINAL SOURCE:
        (A) ORGANISM: Rattus rattus (xi) SEQUENCE DESCRIPTION: SEQ ID NO:6:

```
Met Leu Pro Arg Leu Ser Phe Asn Asn Val Ser Trp Thr Leu Leu Tyr
 1               5                  10                  15
Tyr Leu Phe Ile Phe Gln Val Arg Gly Glu Asp Ser Gln Lys Ala Val
            20                  25                  30
Pro Ser Thr Arg Thr Ser Cys Pro Met Gly Ser Lys Ala Tyr Arg Ser
                35                  40                  45
Tyr Cys Tyr Thr Leu Val Thr Thr Leu Lys Ser Trp Phe Gln Ala Asp
        50                  55                  60
Leu Ala Cys Gln Lys Arg Pro Ser Gly His Leu Val Ser Ile Leu Ser
 65                  70                  75                  80
Gly Gly Glu Ala Ser Phe Val Ser Ser Leu Val Thr Gly Arg Val Asn
                85                  90                  95
```

-continued

```
Asn  Asn  Gln  Asp  Ile  Trp  Ile  Trp  Leu  His  Asp  Pro  Thr  Met  Gly  Gln
               100                      105                      110

Gln  Pro  Asn  Gly  Gly  Gly  Trp  Glu  Trp  Ser  Asn  Ser  Asp  Val  Leu  Asn
          115                      120                      125

Tyr  Leu  Asn  Trp  Asp  Gly  Asp  Pro  Ser  Ser  Thr  Val  Asn  Arg  Gly  Asn
     130                      135                      140

Cys  Gly  Ser  Leu  Thr  Ala  Thr  Ser  Glu  Phe  Leu  Lys  Trp  Gly  Asp  His
145                      150                      155                      160

His  Cys  Asp  Val  Glu  Leu  Pro  Phe  Val  Cys  Lys  Phe  Lys  Gln
               165                      170
```

( 2 ) INFORMATION FOR SEQ ID NO:7:

( i ) SEQUENCE CHARACTERISTICS:
        ( A ) LENGTH: 165 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Rattus rattus ( x i ) SEQUENCE DESCRIPTION: SEQ ID NO:7:

```
Met  Thr  Arg  Asn  Lys  Tyr  Phe  Ile  Leu  Leu  Ser  Cys  Leu  Met  Val  Leu
1                   5                        10                       15

Ser  Pro  Ser  Gln  Gly  Gln  Glu  Ala  Glu  Glu  Asp  Leu  Pro  Ser  Ala  Arg
               20                       25                       30

Ile  Thr  Cys  Pro  Glu  Gly  Ser  Asn  Ala  Tyr  Ser  Ser  Tyr  Cys  Tyr  Tyr
          35                       40                       45

Phe  Met  Glu  Asp  His  Leu  Ser  Trp  Ala  Glu  Ala  Asp  Leu  Phe  Cys  Gln
     50                       55                       60

Asn  Met  Asn  Ser  Gly  Tyr  Leu  Val  Ser  Val  Leu  Ser  Gln  Ala  Glu  Gly
65                       70                       75                       80

Asn  Phe  Leu  Ala  Ser  Leu  Ile  Lys  Glu  Ser  Gly  Thr  Thr  Ala  Ala  Asn
                    85                       90                       95

Val  Trp  Ile  Gly  Leu  His  Asp  Pro  Lys  Asn  Asn  Arg  Arg  Trp  His  Trp
               100                      105                      110

Ser  Ser  Gly  Ser  Leu  Phe  Leu  Tyr  Lys  Ser  Trp  Asp  Thr  Gly  Tyr  Pro
          115                      120                      125

Asn  Asn  Ser  Asn  Arg  Gly  Tyr  Cys  Val  Ser  Val  Thr  Ser  Asn  Ser  Gly
     130                      135                      140

Tyr  Lys  Lys  Trp  Arg  Asp  Asn  Ser  Cys  Asp  Ala  Gln  Leu  Ser  Phe  Val
145                      150                      155                      160

Cys  Lys  Phe  Lys  Ala
               165
```

INGAP PROTEIN INVOLVED IN PANCREATIC ISLET NEOGENESIS

BACKGROUND OF THE INVENTION

Pancreatic islets of Langerhans are the only organ of insulin production in the body. However, they have a limited capacity for regeneration. This limited regeneration capacity predisposes mammals to develop diabetes mellitus. Thus there is a need in the art of endocrinology for products which can stimulate the regeneration of islets of Langerhans to prevent or ameliorate the symptoms of diabetes mellitus.

One model of pancreatic islet cell regeneration involves cellophane-wrapping of the pancreas in the Syrian golden hamster (1). Wrapping of the pancreas induces the formation of new endocrine cells which appear to arise from duct epithelium (2-4). There is a need in the art to identify and isolate the factor(s) which is responsible for islet cell regeneration.

SUMMARY OF THE INVENTION

It is an object of the invention to provide a preparation of a mammalian protein or polypeptide portions thereof involved in islet cell neogenesis.

It is another object of the invention to provide a DNA molecule encoding a mammalian protein involved in islet cell neogenesis.

It is yet another object of the invention to provide a preparation of a mammalian INGAP (islet neogenesis associated protein) protein.

It is still another object of the invention to provide nucleotide probes for detecting mammalian genes involved in islet cell neogenesis.

It is an object of the invention to provide a method for isolation of INGAP genes from a mammal.

It is another object of the invention to provide an antibody preparation which is specifically immunoreactive with an INGAP protein.

It is yet another object of the invention to provide methods of producing INGAP proteins.

It is an object of the invention to provide methods for treating diabetic mammals.

It is another object of the invention to provide methods for growing pancreatic islet cells in culture.

It is still another object of the invention to provide methods of enhancing the life span of pancreatic islet cells encapsulated in polycarbon shells.

It is an object of the invention to provide methods of enhancing the number of pancreatic islet cells in a mammal.

It is an object of the invention to provide transgenic mammals.

It is another object of the invention to provide genetically engineered mammals.

It is yet another object of the invention to provide methods of identifying individual mammals at risk for diabetes.

It is an object of the invention to provide methods of detecting INGAP protein in a sample from a mammal.

It is still another object of the invention to provide a method of treating isolated islet cells to avoid apoptosis.

It is another object of the invention to provide methods of treating mammals receiving islet cell transplants.

It is an object of the invention to provide a method of inducing differentiation of β cell progenitors.

It is an object of the invention to provide a method of identifying β cell progenitors.

It is another object of the invention to provide a method of treating a mammal with pancreatic endocrine failure.

It is an object of the invention to provide antisense constructs for regulating the expression of INGAP.

It is yet another object of the invention to provide a method for treating nesidioblastosis.

It is still another object of the invention to provide kits for detecting mammalian INGAP proteins.

It is an object of the invention to provide pharmaceutical compositions for treatment of pancreatic insufficiency.

These and other objects of the invention are provided by one or more of the embodiments described below.

In one embodiment a preparation of a mammalian INGAP protein is provided. The preparation is substantially free of other mammalian proteins.

In another embodiment an isolated cDNA molecule is provided. The cDNA molecule encodes a mammalian INGAP protein.

In still another embodiment of the invention a preparation of a mammalian INGAP protein is provided. The preparation is made by the process of:

inducing mammalian pancreatic cells to express INGAP protein by cellophane-wrapping; and purifying said INGAP protein from said induced mammalian pancreatic cells.

In yet another embodiment of the invention a nucleotide probe is provided. The probe comprises at least 20 contiguous nucleotides of the sequence shown in SEQ ID NO: 1.

In another embodiment of the invention a preparation of INGAP protein of a mammal is provided. The preparation is substantially purified from other proteins of the mammal. The INGAP protein is inducible upon cellophane-wrapping of pancreas of the mammal.

In yet another embodiment of the invention a method of isolating an INGAP gene from a mammal is provided. The method comprises:

hybridizing one or more oligonucleotides comprising at least 10 contiguous nucleotides of the sequence shown in SEQ ID NO: 1 to genomic DNA or cDNA of said mammal;

identifying DNA molecules from said genomic DNA or cDNA which hybridize to said one or more oligonucleotides.

In still another embodiment of the invention an isolated cDNA molecule is provided. The cDNA molecule is obtained by the process of:

hybridizing one or more oligonucleotides comprising at least 10 contiguous nucleotides of the sequence shown in SEQ ID NO: 1 to genomic DNA or cDNA of said mammal;

identifying DNA molecules from said genomic DNA or cDNA which hybridize to said one or more oligonucleotides.

In another embodiment of the invention an antibody is provided. The antibody is specifically immunoreactive with a mammalian INGAP protein.

According to still another embodiment of the invention a method of producing a mammalian INGAP protein is provided. The method comprises the steps of:

providing a host cell transformed with a cDNA encoding a mammalian INGAP protein;

culturing the host cell in a nutrient medium so that the INGAP protein is expressed; and harvesting the INGAP protein from the host cell or the nutrient medium.

According to yet another embodiment of the invention a method of producing a mammalian INGAP protein is provided. The method comprises the steps of:

providing a host cell comprising a DNA molecule obtained by the process of:
  hybridizing one or more oligonucleotides comprising at least 10 contiguous nucleotides of the sequence shown in SEQ ID NO: 1 to genomic DNA or cDNA of said mammal;
  identifying DNA molecules from said genomic DNA or cDNA which hybridize to said one or more oligonucleotides;
  culturing the host cell in a nutrient medium so that the mammalian INGAP protein is expressed; and
  harvesting the mammalian INGAP protein from the host cells or the nutrient medium.

According to another embodiment of the invention a method of treating diabetic mammals is provided. The method comprises:
  administering to a diabetic mammal a therapeutically effective amount of an INGAP protein to stimulate growth of islet cells.

According to another embodiment of the invention a method of growing pancreatic islet cells in culture is provided. The method comprises:
  supplying an INGAP protein to a culture medium for growing pancreatic islet cells; and
  growing islet cells in said culture medium comprising INGAP protein.

According to another embodiment of the invention a method of enhancing the life span of pancreatic islet cells encapsulated in a polycarbon shell is provided. The method comprises:
  adding to encapsulated pancreatic islet cells an INGAP protein in an amount sufficient to enhance the survival rate or survival time of said pancreatic islet cells.

According to another embodiment of the invention a method of enhancing the number of pancreatic islet cells in a mammal is provided. The method comprises:
  administering a DNA molecule which encodes an INGAP protein to a pancreas in a mammal.

According to another embodiment of the invention a method of enhancing the number of pancreatic islet cells in a mammal is provided. The method comprises:
  administering an INGAP protein to a pancreas in a mammal.

According to another embodiment of the invention a transgenic mammal is provided. The mammal comprises an INGAP gene of a second mammal.

According to another embodiment of the invention a non-human mammal is provided. The mammal has been genetically engineered to contain an insertion or deletion mutation of an INGAP gene of said mammal.

According to another embodiment of the invention a method of identifying individual mammals at risk for diabetes is provided. The method comprises:
  identifying a mutation in an INGAP gene of a sample of an individual mammal, said mutation causing a structural abnormality in an INGAP protein encoded by said gene or causing a regulatory defect leading to diminished or obliterated expression of said INGAP gene.

According to another embodiment of the invention a method of detecting INGAP protein in a sample from a mammal is provided. The method comprises:
  contacting said sample with an antibody preparation which is specifically immunoreactive with a mammalian INGAP protein.

According to another embodiment of the invention a method of treating isolated islet cells of a mammal to avoid apoptosis of said cells is provided. The method comprises:
  contacting isolated islet cells of a mammal with a preparation of a mammalian INGAP protein, substantially purified from other mammalian proteins, in an amount sufficient to increase the survival rate of said isolated islet cells.

According to another embodiment of the invention a method of treating a mammal receiving a transplant of islet cells is provided. The method comprises:
  administering a preparation of a mammalian INGAP protein to a mammal receiving a transplant of islet cells, wherein said step of administering is performed before, during, or after said transplant.

According to another embodiment of the invention a method of inducing differentiation of β cell progenitors is provided. The method comprises:
  contacting a culture of pancreatic duct cells comprising β cell progenitors with a preparation of a mammalian INGAP protein substantially free of other mammalian proteins, to induce differentiation of said β cell progenitors.

In yet another embodiment of the invention a method is provided for identification of β cell progenitors. The method comprises:
  contacting a population of pancreatic duct cells with a mammalian INGAP protein; and
  detecting cells among said population to which said INGAP protein specifically binds.

According to another embodiment of the invention a method of treating a mammal with pancreatic endocrine failure is provided. The method comprises:
  contacting a preparation of pancreatic duct cells comprising β cell progenitors isolated from a mammal afflicted with pancreatic endocrine failure with a preparation of a mammalian INGAP protein substantially free of other mammalian proteins to induce differentiation of said β cell progenitors; and
  autologously transplanting said treated pancreatic duct cells into said mammal.

According to another embodiment of the invention an antisense construct of a mammalian INGAP gene is provided. The construct comprises:
  a promoter, a terminator, and a nucleotide sequence consisting of a mammalian INGAP gene, said nucleotide sequence being between said promoter and said terminator, said nucleotide sequence being inverted with respect to said promoter, whereby upon expression from said promoter an mRNA complementary to native mammalian INGAP mRNA is produced.

According to another embodiment of the invention a method of treating nesidioblastosis is provided. The method comprises:
  administering to a mammal with nesidioblastosis an antisense construct as described above, whereby overgrowth of β cells of said mammal is inhibited.

According to another embodiment of the invention a kit for detecting a mammalian INGAP protein in a sample from a mammal is provided. The kit comprises:
  an antibody preparation which is specifically immunoreactive with a mammalian INGAP protein; and
  a polypeptide which comprises a sequence of at least 15 consecutive amino acids of a mammalian INGAP protein.

According to another embodiment of the invention a pharmaceutical composition for treatment of pancreatic insufficiency is provided. The composition comprises:
  a mammalian INGAP protein in a pharmaceutically acceptable diluent or carrier.

According to another embodiment of the invention a pharmaceutical composition is provided. The composition comprises:

a preparation of a polypeptide which comprises a sequence of at least 15 consecutive amino acids of a mammalian INGAP protein and a pharmaceutically acceptable diluent or carrier.

These and other embodiments of the invention provide the art with means of stimulating and inhibiting islet cell neogenesis. Means of diagnosis of subsets of diabetes mellitus are also provided by this invention.

BRIEF DESCRIPTION OF THE DRAWINGS

FIG. 1A and 1B Nucleotide sequence of hamster INGAP SEQ ID NO:1 and deduced sequence of encoded immature protein SEQ ID NO:2. The non-coding sequences are in lower case letters, and the polyadenylation signal is underlined.

FIG. 2. Comparison of amino acid sequences of INGAP SEQ ID NO:2, rat PAP-I (PAP-I) (18) SEQ ID NO: 3, Human PAP/HIP (PAP-H/HIP)(10, 11) SEQ ID NO:4, rat PAP-III (PAP-III)(9) SEQ ID NO: 5, rat PAP-II (PAP-II)(8) SEQ ID NO:6, Rat Reg/PSP/Lithostatine (REG/LITH)(13, 15) SEQ ID NO: 7 and the invariable motif found by Drickamer in all members of C-type lectins (Drickamer) (12). Six conserved cysteines are marked by asterisks and the 2 putative N-glycosylation sites of INGAP are underlined and in bold letters.

DETAILED DESCRIPTION OF THE PREFERRED EMBODIMENTS

Figure 3A:
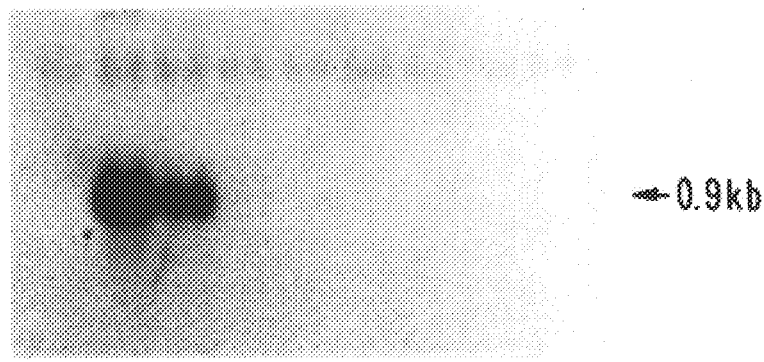
FIGS. 3A and 3C. Northern blot analysis of INGAP and amylase gene expression -in pancreatic tissue from control and wrapped hamster pancreas. 30 g of heat denatured total RNA was separated by electrophoresis on a 1.2% agarose, 0.6% formaldehyde/MOPS denaturing gel, and transferred to nylon membrane. Membranes were hybridized with a 747 bp hamster INGAP cDNA probe (cloned in our lab) (A), a 1000 bp rat amylase cDNA probe (generously given by Chris Newgard Dallas, Texas) (13) and with an 18S ribosomal 24mer synthetic oligonucleotide probe to control for RNA integrity and loading (C).

We now report the identification of a gene, INGAP, that shows striking homology to the pancreatitis associated protein (PAP) family of genes (7–11). The predicted protein shares the carbohydrate recognition domain (CRD) of the calcium dependent C-type lectins as defined by Drickamer (12). INGAP protein plays a role in stimulation of islet neogenesis, in particular, in beta cell regeneration from ductal cells.

The cDNA sequence of a mammalian INGAP is provided in SEQ ID NO: 1. The predicted amino acid sequence is shown in SEQ ID NO:2. These sequences were determined from nucleic acids isolated from hamster, but it is believed that other mammalian species will contain INGAP genes which are quite similar. For example, one would expect homologous genes to contain at least about 70% identity. Closer species would be expected to have at least about 75%, 80%, or even 85% identity. In contrast, other family members of the calcium dependent C-type lectins contain at most 60% identity with INGAP.

The DNA sequence provided herein can be used to form vectors which will replicate the gene in a host cell, and may also express INGAP protein. DNA sequences which encode the same amino acid sequence as shown in SEQ ID NO:2 can also be used, without departing from the contemplation of the invention. DNA sequences coding for other mammalian INGAPs are also within the contemplation of the invention. Suitable vectors, for both prokaryotic and eukaryotic cells, are known in the art. Some vectors are specifically designed to effect expression of inserted DNA segments downstream from a transcriptional and translational control site. One such vector for expression in eukaryotic cells employs EBNA His, a plasmid which is available commercially from InVitrogen Corp. The loaded vector produces a fusion protein comprising a portion of a histidine biosynthetic enzyme and INGAP. Another vector, which is suitable for use in prokaryotic cells, is pCDNA3. Selection of a vector for a particular purpose may be made using knowledge of the properties and features of the vectors, such as useful expression control sequences. Vectors may be used to transform or transfect host cells, either stably or transiently. Methods of transformation and transfection are known in the art, and may be used according to suitability for a particular host cell. Host cells may be selected according to the purpose of the transfection. A suitable prokaryotic host is $E.\ coli$ DH5α. A suitable eukaryotic host is cos7, an African Green Monkey kidney cell line. For some purposes, proper glycosylation of INGAP may be desired, in which case a suitable host cell should be used which recognizes the glycosylation signal of INGAP.

Probes comprising at least 10, 15, 20, or 30 nucleotides of contiguous sequence according to SEQ ID NO: 1 can be used for identifying INGAP genes in particular individuals or in members of other species. Appropriate conditions for hybridizations to same or different species' DNA are known in the art as high stringency and low stringency, respectively. These can be used in a variety of formats according to the desired use. For example, Southern blots, Northern blots, and in situ colony hybridization, can be used as these are known in the art. Probes typically are DNA or RNA oligomers of at least 10, 15, 20, or 30 nucleotides. The probe may be labeled with any detectable moiety known in the art, including radiolabels, fluorescent labels, enzymes, etc. Probes may also be derived from other mammalian INGAP gene sequences.

INGAP genes can be isolated from other mammals by utilizing the nucleotide sequence information provided herein. (More laboriously, they can be isolated using the same method described in detail below for isolation of the hamster INGAP gene.) Oligonucleotides comprising at least 10 contiguous nucleotides of the disclosed nucleotide sequence of INGAP are hybridized to genomic DNA or cDNA of the mammal. The DNA may conveniently be in the form of a library of clones. The oligonucleotides may be labelled with any convenient label, such as a radiolabel or an enzymatic or fluorescence label. DNA molecules which hybridize to the probe are isolated. Complete genes can be constructed by isolating overlapping DNA segments, for example using the first isolated DNA as a probe to contiguous DNA in the library or preparation of the mammal's DNA. Confirmation of the identity of the isolated DNA can be made by observation of the pattern of expression of the gene in the pancreas when subjected to cellophane wrapping, for example. Similarly, the biological effect of the encoded product upon pancreatic ductal cells will also serve to identify the gene as an INGAP gene.

If two oligonucleotides are hybridized to the genomic DNA or cDNA of the mammal then they can be used a primers for DNA synthesis, for example using the polymerase chain reaction or the ligase chain reaction. Construction of a full-length gene and confirmation of the identity of the isolated gene can be performed as described above.

INGAP protein may be isolated according to the invention by inducing mammalian pancreatic cells to express INGAP protein by means of cellophane-wrapping. This technique is described in detail in reference no. 1 which is expressly incorporated herein. Briefly, the pancreas is exposed and a strip of sterile cellophane tape is wrapped carefully around the head of the gland, so as not to crush the underlying tissue. Duct ligation is not involved. INGAP protein so produced may be purified from other mammalian proteins by means of immunoaffinity techniques, for example, or other techniques known in the art of protein purification. An antibody specific for a mammalian INGAP is produced using all, or fragments of, the amino acid sequence of an INGAP protein, such as shown in SEQ ID NO: 2, as immunogens. The immunogens can be used to identify and purify immunoreactive antibodies. Monoclonal or polyclonal antibodies can be made as is well known in the art. The antibodies can be conjugated to other moieties, such as detectable labels or solid support materials. Such antibodies can be used to purify proteins isolated from mammalian pancreatic cells or from recombinant cells. Hybridomas which secrete specific antibodies for an INGAP protein are also within the contemplation of the invention.

Host cells as described above can be used to produce a mammalian INGAP protein. The host cells comprise a DNA molecule encoding a mammalian INGAP protein. The DNA can be according to SEQ ID NO:1, or isolated from other mammals according to methods described above. Host cells can be cultured in a nutrient medium under conditions where INGAP protein is expressed. INGAP protein can be isolated from the host cells or the nutrient medium, if the INGAP protein is secreted from the host cells.

It has now been found that INGAP and fragments thereof are capable of inducing and stimulating islet cells to grow. Moreover, they are capable of inducing differentiation of pancreatic duct cells, and of allowing such cells to avoid the apoptotic pathway. Thus many therapeutic modalities are now possible using INGAP, fragments thereof, and nucleotide sequences encoding INGAP. Therapeutically effective amounts of INGAP are supplied to patient pancreata, to isolated islet cells, and to encapsulated pancreatic islet cells, such as in a polycarbon shell. Suitable amounts of INGAP for therapeutic purposes range from 1–150 μg/kg of body weight or in vitro from 1–10,000 μg/ml. Optimization of such dosages can be ascertained by routine testing. Methods of administering INGAP to mammals can be any that are known in the art, including subcutaneous, via the portal vein, by local perfusion, etc.

Conditions which can be treated according to the invention by supplying INGAP include diabetes mellitus, both insulin dependent and non-insulin dependent, pancreatic insufficiency, pancreatic failure, etc. Inhibition of INGAP expression can be used to treat nesidioblastosis.

According to the present invention, it has now been found that a small portion of INGAP is sufficient to confer biological activity. A fragment of 20 amino acids of the sequence of SEQ ID NO: 2, from amino acid #103–#122 is sufficient to stimulate pancreatic ductal cells to grow and proliferate. The effect has been seen on a rat tumor duct cell line, a hamster duct cell line, a hamster insulinoma cell line, and a rat insulinoma cell line. The analogous portions of other mammalian INGAP proteins are quite likely to have the same activity. This portion of the protein is not similar to other members of the pancreatitis associated protein (PAP) family of proteins. It contains a glycosylation site and it is likely to be a primary antigenic site of the protein as well. This fragment has been used to immunize mice to generate monoclonal antibodies.

The physiological site of expression of INGAP has been determined. INGAP is expressed in acinar tissue, in the exocrine portion of the pancreas. It is not expressed in ductal or islet cells, i. e., the paracrine portion of the pancreas. Expression occurs within 24–48 hours of induction by means of cellophane wrapping.

Transgenic animals according to the present invention are mammals which carry an INGAP gene from a different mammal. The transgene can be expressed to a higher level than the endogenous INGAP genes by judicious choice of transcription regulatory regions. Methods for making transgenic animals are well-known in the art, and any such method can be used. Animals which have been genetically engineered to carry insertions, deletions, or other mutations which alter the structure of the INGAP protein or regulation of expression of INGAP are also contemplated by this invention. The techniques for effecting these mutations are known in the art.

Diagnostic assays are also contemplated within the scope of the present invention. Mutations in INGAP can be ascertained in samples such as blood, amniotic fluid, chorionic villus, blastocyst, and pancreatic cells. Such mutations identify individuals who are at risk for diabetes. Mutations can be identified by comparing the nucleotide sequence to a wild-type sequence of an INGAP gene. This can be accomplished by any technique known in the art, including comparing restriction fragment length polymorphisms, comparing polymerase chain reaction products, nuclease protection assays, etc. Alternatively, altered proteins can be identified, e.g., immunologically or biologically.

The present invention also contemplates the use of INGAP antisense constructs for treating nesidioblastosis, a condition characterized by overgrowth of β cells. The antisense construct is administered to a mammal having nesidioblastosis, thereby inhibiting the overgrowth of β cells. An antisense construct typically comprises a promoter, a terminator, and a nucleotide sequence consisting of a mammalian INGAP gene. The INGAP sequence is between the promoter and the terminator and is inverted with respect to the promoter as it is expressed naturally. Upon expression from the promoter, an mRNA complementary to native mammalian INGAP is produced.

Immunological methods for assaying INGAP in a sample from a mammal are useful, for example, to monitor the therapeutic administration of INGAP. Typically an antibody specific for INGAP will be contacted with the sample and the binding between the antibody and any INGAP in the sample will be detected. This can be by means of a competitive binding assay, in which the incubation mixture is spiked with a known amount of a standard INGAP preparation, which may conveniently be detectably labeled. Alternatively, a polypeptide fragment of INGAP may be used as a competitor. In one particular assay format, the antibodies are bound to a solid phase or support, such as a bead, polymer matrix, or a microtiter plate.

According to the present invention, pancreatic duct cells of a mammal with pancreatic endocrine failure can be removed from the body and treated in vitro. The duct cells typically comprise β cell progenitors. Thus treatment with a preparation of a mammalian INGAP protein will induce differentiation of the β cell progenitors. The duct cells are contacted with a preparation of a mammalian INGAP protein substantially free of other mammalian proteins. The treated cells can then used as an autologous transplant into the mammal from whom they were derived. Such an autologous treatment minimizes adverse host versus graft reactions involved in transplants.

INGAP protein can also be used to identify those cells which bear receptors for INGAP. Such cells are likely to be the β cell progenitors, which are sensitive to the biological effects of INGAP. INGAP protein can be detectably labeled, such as with a radiolabel or a fluorescent label, and then contacted with a population of cells from the pancreatic duct. Cells which bind to the labeled protein will be identified as those which bear receptors for INGAP, and thus are β cell progenitors. Fragments of INGAP can also be used for this purpose, as can immobilized INGAP which can be used to separate cells from a mixed population of cells to a solid support. INGAP can be immobilized to solid phase or support by adsorption to a surface, by means of an antibody, or by conjugation. Any other means as is known in the art can also be used.

Kits are provided by the present invention for detecting a mammalian INGAP protein in a sample. This may be useful, inter alia, for monitoring metabolism of INGAP during therapy which involves administration of INGAP to a mammal. The kit will typically contain an antibody preparation which is specifically immunoreactive with a mammalian INGAP protein. The antibodies may be polyclonal or monoclonal. If polyclonal they may be affinity purified to render them monospecific. The kit will also typically contain a polypeptide which has at least 15 consecutive amino acids of a mammalian INGAP protein. The polypeptide is used to compete with the INGAP protein in a sample for binding to the antibody. Desirably the polypeptide will be detectably labeled. The polypeptide will contain the portion of INGAP to which the antibody binds. Thus if the antibody is monoclonal, the polypeptide will successfully compete with INGAP by virtue of it containing the epitope of the antibody. It may also be desirable that the antibodies be bound to a solid phase or support, such as polymeric beads, sticks, plates, etc.

Pharmaceutical compositions containing a mammalian INGAP protein may be used for treatment of pancreatic insufficiency. The composition may alternatively contain a polypeptide which contains a sequence of at least 15 consecutive amino acids of a mammalian INGAP protein. The polypeptide will contain a portion of INGAP which is biologically active in the absence of the other portions of the protein. The polypeptide may be part of a larger protein, such as a genetic fusion with a second protein or polypeptide. Alternatively, the polypeptide may be conjugated to a second protein, for example, by means of a cross-linking agent. Suitable portions of INGAP proteins may be determined by homology with amino acids #103 to #122 of SEQ ID NO:2, or by the ability of test polypeptides to stimulate pancreatic duct cells to grow and proliferate. As is known in the art, it is often the case that a relatively small number of amino acids can be removed from either end of a protein without destroying activity. Thus it is contemplated within the scope of the invention that up to about 10% of the protein can be deleted, and still provide essentially all functions of INGAP. Such proteins have at least about 130 amino acids, in the case of hamster INGAP.

The pharmaceutical composition will contain a pharmaceutically acceptable diluent or carrier. A liquid formulation is generally preferred. INGAP may be formulated at different concentrations or using different formulants. For example, these formulants may include oils, polymers, vitamins, carbohydrates, amino acids, salts, buffers, albumin, surfactants, or bulking agents. Preferably carbohydrates include sugar or sugar alcohols such as mono-, di-, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution, if these are used. Most any physiological buffer may be used, but citrate, phosphate, succinate, and glutamate buffers or mixtures thereof are preferred. Preferably, the concentration is from 0.01 to 0.3 molar. Surfactants can also be added to the formulation.

Additionally, INGAP or polypeptide portions thereof can be chemically modified by covalent conjugation to a polymer to increase its circulating half-life, for example. Preferred polymers, and methods to attach them to peptides, are shown in U.S. Pat. Nos. 4,766,106, 4,179,337, 4,495,285, and 4,609,546. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

The following examples are not intended to limit the scope of the invention, but merely to exemplify that which is taught above.

EXAMPLES

Example 1

This example describes the cloning and isolation of a cDNA encoding a novel, developmentally regulated, pancreatic protein.

We hypothesized that a unique locally produced factor(s) is responsible for islet cell regeneration. Using the recently developed mRNA differential display technique (5,6) to compare genes differentially expressed in cellophane wrapped (CW) versus control pancreata (CP) allowed us to identify a cDNA clone (RD19-2) which was uniquely expressed in cellophane wrapped pancreas.

A cDNA library was constructed from mRNA isolated from cellophane wrapped hamster pancreas using oligo d(T) primed synthesis, and ligation into pcDNA3 vector (Invitrogen). The number of primary recombinants in the library was $1.2 \times 10^6$ with an average size of 1.1 kb. The cDNA library was screened for clones of interest using high density colony plating techniques. Colonies were lifted onto nylon membranes (Schleicher & Schuell) and further digested with proteinase K (50(g/ml). Treated membranes were baked at 80° C. for 1 hour and hybridized at 50° C. for 16–18 hours with $1-5 \times 10^6$ cpm/ml of [($^{32}$P)-dCTP(Dupont-NewEngland Nuclear) radiolabeled RD19-2 probe. Colonies with a positive hybridization signal were isolated, compared for size with Northern mRNA transcript, and sequenced to confirm identity with the RD19-2 sequence.

Example 2

This example compares the sequence of INGAP to other proteins with which it shares homology.

The nucleotide sequence of the hamster INGAP clone with the longest cDNA insert was determined. As shown in FIGS. 1A and 1B the hamster cDNA comprises 747 nucleotides (nt), exclusive of the poly(A) tail and contains a major open reading frame encoding a 175 amino acid protein. The open reading frame is followed by a 3'-untranslated region of 206 nt. A typical polyadenylation signal is present 11 nt upstream of the poly(A) tail. The predicted INGAP protein shows structural homology to both the PAP/HIP family of genes which is associated with pancreatitis or liver adenocarcinoma (7–11) and the Reg/PSP/lithostatine family of genes (13,15) which has been shown to stimulate pancreatic beta-cell growth (14) and might play a role in pancreatic islet regeneration. Comparison of the nucleotide sequence and their deduced amino acids between hamster INGAP and rat PAP-I shows a high degree of homology in the coding region (60 and 58 % in nucleotide and amino acid sequences, respectively). The predicted amino acid sequence of the hamster INGAP reveals 45 % identity to PAP II and 50% to PAP III both of which have been associated with acute pancreatitis, and 54% to HIP which was found in a hepatocellular carcinoma. INGAP also shows 40% identity to the rat Reg/PSP/lithostatine protein (FIG. 2). Reg is thought to be identical to the pancreatic stone protein (PSP) (15,16) or pancreatic thread protein (PTP) (17). The N-terminus of the predicted sequence of INGAP protein is highly hydrophobic which makes it a good candidate for being the signal peptide which would allow the protein to be secreted. Similar to PAP/HIP but different from the Reg/PSP/lithostatine proteins a potential N-glycosylation site is situated at position 135 of the INGAP sequence. Unique to INGAP is another potential N-glycosylation site situated at position 115. INGAP also shows a high degree of homology (12/18) (FIG. 2) with a consensus motif in members of the calcium-dependent (C-type) animal lectin as determined by Drickamer including four perfectly conserved cysteines which form two disulfide bonds (12). Two extra cysteines found at the amino-terminus of INGAP (FIG. 2) are also present in Reg/PSP and PAP/HIP. However, it is not clear what the biological significance might be.

Example 3

This example demonstrates the temporal expression pattern of INGAP upon cellophane-wrapping.

Figure 3B:
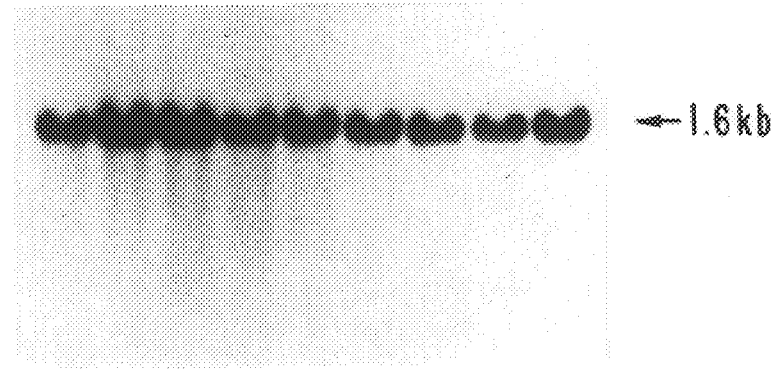
Figure 3C:

In order to determine the temporal expression of the INGAP gene, total RNA extracted from CP and CW pancreas was probed with the hamster INGAP cDNA clone in Northern blot analysis. A strong single transcript of 900 bp was detected (FIGS. 3A, 3B and 3C) 1 and 2 days after cellophane wrapping which disappeared by 6 through 42 days and was absent from CP. INGAP mRNA is associated with CW induced pancreatic islet neogenesis, since it is present only after CW. It is not likely that the increased expression of INGAP is associated with acute pancreatitis as is the case with the PAP family of genes. During the acute phase of pancreatitis the concentrations of most mRNAs encoding pancreatic enzymes including amylase are decreased significantly (16,18). In contrast, in the CW model of islet neogenesis in which high expression of INGAP has been detected, amylase gene expression was simultaneously increased above normal (FIGS. 3A, 3B and 3C) rather than decreased, suggesting that INGAP expression is not associated with pancreatitis but rather with islet neogenesis. The cause of increased amylase gene expression 1 and 2 days after CW is as yet unclear, and more studies need to be done to elucidate this issue. It is unlikely though, that the increase is associated with exocrine cell regeneration which occurs at a later time after CW (19). Thus, INGAP protein plays a role in stimulation of islet neogenesis, in particular, in beta cell regeneration from ductal cells.

References

1. Rosenberg, L., Brown, R. A. and Duguid, W. P. (1982). Surg. Forum 33, 227–230.
2. Rosenberg, L., Brown, R. A. and Duguid, W. P. (1983). J. Surg. Res. 35, 63–72.
3. Rosenberg, L., Duguid, W. P. and Vinik, A. I. (1987). Dig. Dis. Sci. 32, 1185.
4. Clas, D., Rosenberg, L. and Duguid, W. P. (1989). Pancreas 4, 613 (Abstract).
5. Liang, P. and Pardee, B. A. (1992). Science 257, 967–971.
6. Liang, P., Averboukh, L. and Pardee, B. A. (1993). Nucleic Acid Res. 21, 3269–3275.
7. Iovanna, J., Orelle, B., Keim, V. and Dagorn, J. C. (1991). J. Biol. Chem. 266, 24664–24669.
8. Frigerio, J. M., Dusetti, N., Keim, V., Dagorn, J. C. and Iovanna, J. (1993). Biochemistry 32, 9236–9241.
9. Frigerio, J. M., Dusetti, N., Garrido, P., Dagorn, J. C. and Iovanna, J. (1993). Biochim. Biophys. Acta 1216, 329–331.
10. Orelle, B., Keim, V., Masciotra, L., Dagorn, J. C. and Iovanna, J. (1992). J. Clin. Invest. 90, 2284–2291.
11. Lasserre, C., Christa, L., Simon, M. T., Vernier, P. and Brechot, C. (1992). Cancer Res. 52, 5089–5095.
12. Drickamer, K. (1988). J. Biol. Chem. 263, 9557–9560.
13. Terazono, K., Yamamoto, H., Takasawa, S., Shiga, K., Yonemura, Y., Tochino, Y. and Okamoto, H. (1988). J. Biol. Chem. 263, 2111–2114.

14. Watanabe, T., Yutaka, Y., Yonekura, H., Suzuki, Y., Miyashita, H., Sugiyama, K., Morizumi, S., Unno, M., Tanaka, O., Kondo, H., Bone, A. J., Takasawa, S. and Okamoto, H. (1994). Proc. Natl. Acad. Sci. USA 91, 3589–3592.
15. Rouquier, S., Giorgi, D., Iovanna, J. and Dagorn, J. C. (1989). Biochem. J. 264, 621–624.
16. Rouquier, S., Verdier, J., Iovanna, J., Dagorn, J. C. and Giorgi, D. (1991) J. Biol. Chem. 266, 786–791.
17. Gross, J., Carlson, R. I., Brauer, A. W., Margolies, M. N., Warshaw, A. L. and Wands, J. R. (1985). J. Clin. Invest. 76, 2115–2126.
18. Iovanna, J., Keim,V., Michael, R.and Dagorn, J. C. (1991). Am. J. Physiol. 261, G485–G489.
19. Rosenberg, L. and Vinik, A. I. (1989). J. Lab. Clin. Med. 114, 75–83.

We claim:

1. A preparation of a naturally occurring mammalian islet neogenesis associated protein (INGAP protein) substantially free of other mammalian proteins.

2. The preparation of claim 1 wherein the INGAP protein has the amino acid sequence shown in SEQ ID NO: 2.

3. A preparation of a polypeptide which comprises a sequence of at least 15 consecutive amino acids of a naturally occuring mammalian islet neogenesis associated protein (INGAP protein), wherein said polypeptide has immunogenic activity.

4. The preparation of claim 3 wherein said polypeptide is a fusion of said sequence to a second polypeptide derived from a second protein.

5. The preparation of claim 3 wherein said polypeptide is conjugated to a second polypeptide.

6. The preparation of claim 3 wherein said polypeptide is conjugated to a solid support.

7. The preparation of claim 3 wherein said polypeptide has a biological activity of said mammalian INGAP protein.

8. The preparation of claim 7 wherein said biological activity is the ability to stimulate pancreatic duct cells to grow and proliferate.

9. The preparation of claim 3 wherein said polypeptide comprises amino acids #103 to #122 of the mammalian INGAP protein as shown in SEQ ID NO:2.

10. The preparation of claim 3 wherein said polypeptide comprises at least 130 consecutive amino acids of said mammalian INGAP protein as defined by SEQ ID NO:2.

11. A preparation of an islet eogenesis associated protein (INGAP protein) of a mammal substantially purified from other proteins of the mammal wherein said INGAP protein is inducible upon cellophane-wrapping of pancreas of the mammal.

12. A pharmaceutical composition for treatment of pancreatic insufficiency, comprising:
a naturally occuring mammalian islet neogenesis associated protein (INGAP protein) in a pharmaceutically acceptable diluent or carrier.

13. The pharmaceutical composition of claim 12 wherein the INGAP protein has the amino acid sequence shown in SEQ ID NO: 2.

14. A pharmaceutical composition comprising:
a preparation of a polypeptide which comprises a sequence of at least 15 consecutive amino acids of a naturally occurring mammalian islet neogenesis associated protein (INGAP protein) and a pharmaceutically acceptable diluent or carrier, wherein said polypeptide is capable of stimulating β cell regeneration of pancreatic ductal cells.

15. The pharmaceutical composition of claim 14 wherein said polypeptide is a fusion of said sequence to a second polypeptide derived from a second protein.

16. The pharmaceutical composition of claim 14 wherein said polypeptide is conjugated to a second polypeptide.

17. The pharmaceutical composition of claim 14 wherein said polypeptide has a biological activity of said mammalian INGAP protein.

18. The pharmaceutical composition of claim 17 wherein said biological activity is the ability to stimulate pancreatic duct cells to grow and proliferate.

19. The pharmaceutical composition of claim 14 wherein said polypeptide comprises amino acids #103 to #122 of the mammalian INGAP protein as shown in SEQ ID NO:2.

20. The pharmaceutical composition of claim 14 wherein said polypeptide comprises at least 130 consecutive amino acids of said mammalian INGAP protein as defined by SEQ ID NO:2.

21. The preparation of claim 1 which is free of other mammalian proteins.

22. The preparation of claim 11 which is free from other proteins of the mammal.

23. The preparation of claim 11 wherein the INGAP protein has 174 amino acids.

24. The preparation of claim 11 wherein the INGAP protein is purified utilizing antibodies which immunoreact with INGAP.

* * * * *

UNITED STATES PATENT AND TRADEMARK OFFICE
CERTIFICATE OF CORRECTION

PATENT NO.: 5,834,590

DATED: November 10, 1998

INVENTOR(S): Aaron I. VINIK et al.

It is certified that an error appears in the above-identified patent and that said Letters Patent is hereby corrected as shown below:   On the title page: Item [73]

under "Assignee" information, after "Norfolk, Va." add --and McGill University, Montreal, Quebec, Canada--

Signed and Sealed this

Twenty-third Day of May, 2000

Attest:

Q. TODD DICKINSON

*Attesting Officer*         *Director of Patents and Trademarks*